(12) United States Patent
Sullivan et al.

(10) Patent No.: US 10,561,820 B2
(45) Date of Patent: Feb. 18, 2020

(54) HYPOTUBE CONSTRUCTION

(71) Applicants: Gregory Sullivan, Quincy, MA (US);
Stephen Griffin, San Jose, CA (US)

(72) Inventors: Gregory Sullivan, Quincy, MA (US);
Stephen Griffin, San Jose, CA (US)

(73) Assignee: Micro Medical Solutions, Inc.,
Wilmington, MA (US)

( * ) Notice: Subject to any disclaimer, the term of this patent is extended or adjusted under 35 U.S.C. 154(b) by 0 days.

(21) Appl. No.: 15/500,126

(22) PCT Filed: Jul. 29, 2015

(86) PCT No.: PCT/US2015/042676
§ 371 (c)(1),
(2) Date: Jan. 30, 2017

(87) PCT Pub. No.: WO2016/019028
PCT Pub. Date: Feb. 4, 2016

(65) Prior Publication Data
US 2017/0274179 A1 Sep. 28, 2017

Related U.S. Application Data

(60) Provisional application No. 62/055,712, filed on Sep. 26, 2014, provisional application No. 62/030,435, filed on Jul. 29, 2014.

(51) Int. Cl.
*A61M 25/00* (2006.01)
*A61L 29/08* (2006.01)
*A61L 29/14* (2006.01)
*A61M 25/09* (2006.01)
(Continued)

(52) U.S. Cl.
CPC ....... *A61M 25/0054* (2013.01); *A61L 29/085* (2013.01); *A61L 29/14* (2013.01); *A61M 25/0013* (2013.01); *A61M 25/0045* (2013.01); *A61M 25/09* (2013.01); *A61F 2/958* (2013.01);
(Continued)

(58) Field of Classification Search
CPC .. A61M 25/10; A61M 25/0013; A61M 25/09; A61M 25/0045; A61M 25/0054; A61M 2025/0046
See application file for complete search history.

(56) References Cited

U.S. PATENT DOCUMENTS 5,169,386 A * 12/1992 Becker ............... A61F 2/04
600/435
7,989,042 B2   8/2011 Obara
(Continued)

FOREIGN PATENT DOCUMENTS

WO   2006/058234 A2   6/2006

*Primary Examiner* — Theodore J Stigell
(74) *Attorney, Agent, or Firm* — Bay State IP, LLC

(57) ABSTRACT

A medical device such as a catheter may have an elongate shaft that includes a hypotube having a cut formed therein. The elongate shaft may define a lumen that extends within the elongate shaft. A polymer may be disposed over at least a portion of the hypotube. A medical device may include a cut hypotube having a constant pitch and may be configured to reversibly and temporarily alter the pitch of at least a portion of the cut hypotube. In some cases, the medical device may be configured to reversibly and/or temporarily alter a compressive strength of at least a portion of the cut hypotube.

12 Claims, 11 Drawing Sheets

(51) Int. Cl.
*A61F 2/958* (2013.01)
*A61M 25/10* (2013.01)

(52) U.S. Cl.
CPC .......... *A61L 2400/10* (2013.01); *A61M 25/10* (2013.01); *A61M 2025/0046* (2013.01)

(56) References Cited

U.S. PATENT DOCUMENTS

| | | |
|---|---|---|
| 2003/0093059 A1* | 5/2003 | Griffin .............. A61M 25/0045 604/525 |
| 2006/0129176 A1 | 6/2006 | Griffin et al. |
| 2007/0112331 A1 | 5/2007 | Weber et al. |
| 2009/0043283 A1 | 2/2009 | Turnlund |
| 2013/0046285 A1 | 2/2013 | Griffin |
| 2014/0046297 A1* | 2/2014 | Shimada ................ A61L 29/02 604/508 |
| 2014/0107681 A1 | 4/2014 | Davies et al. |

\* cited by examiner

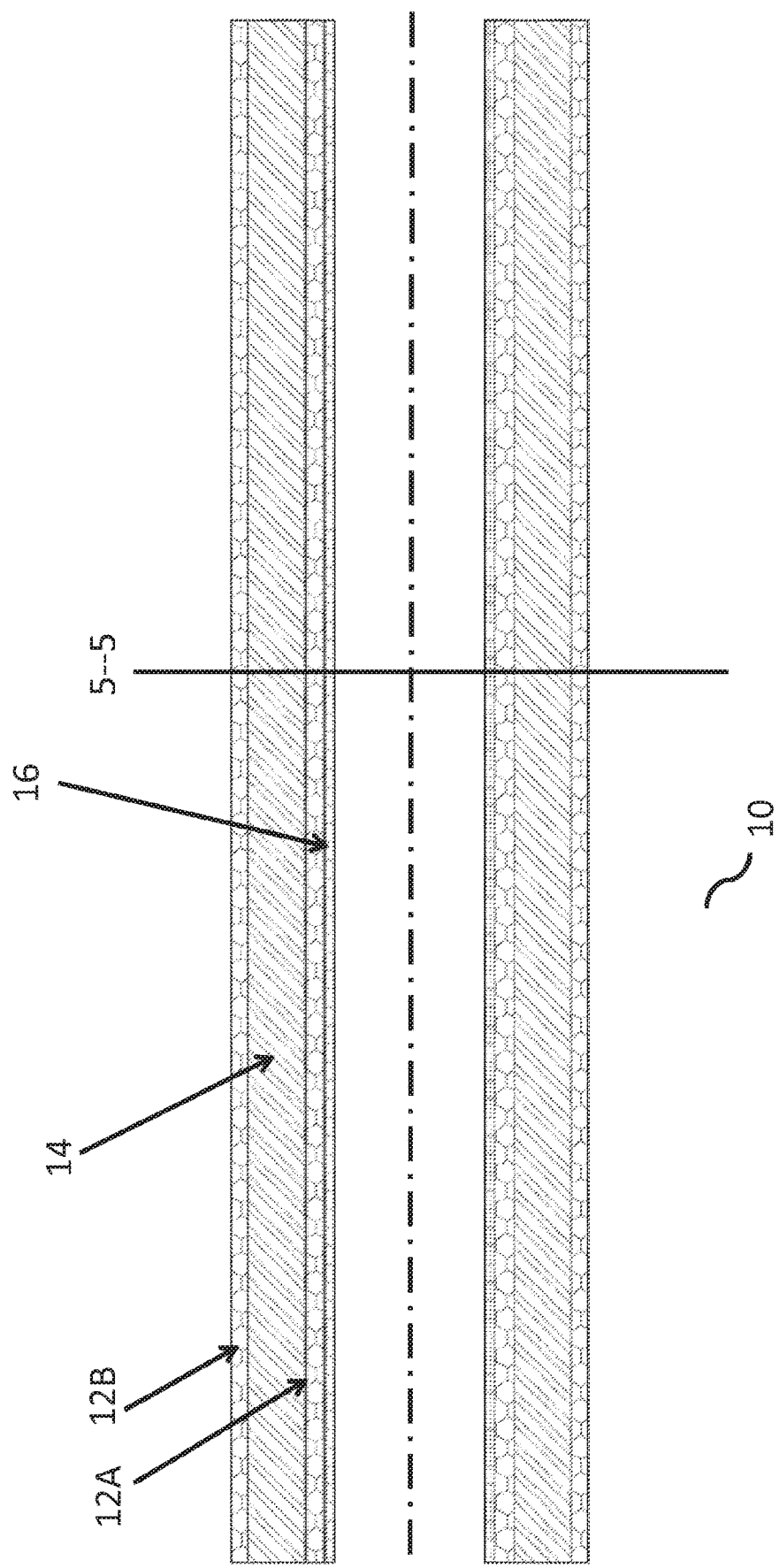

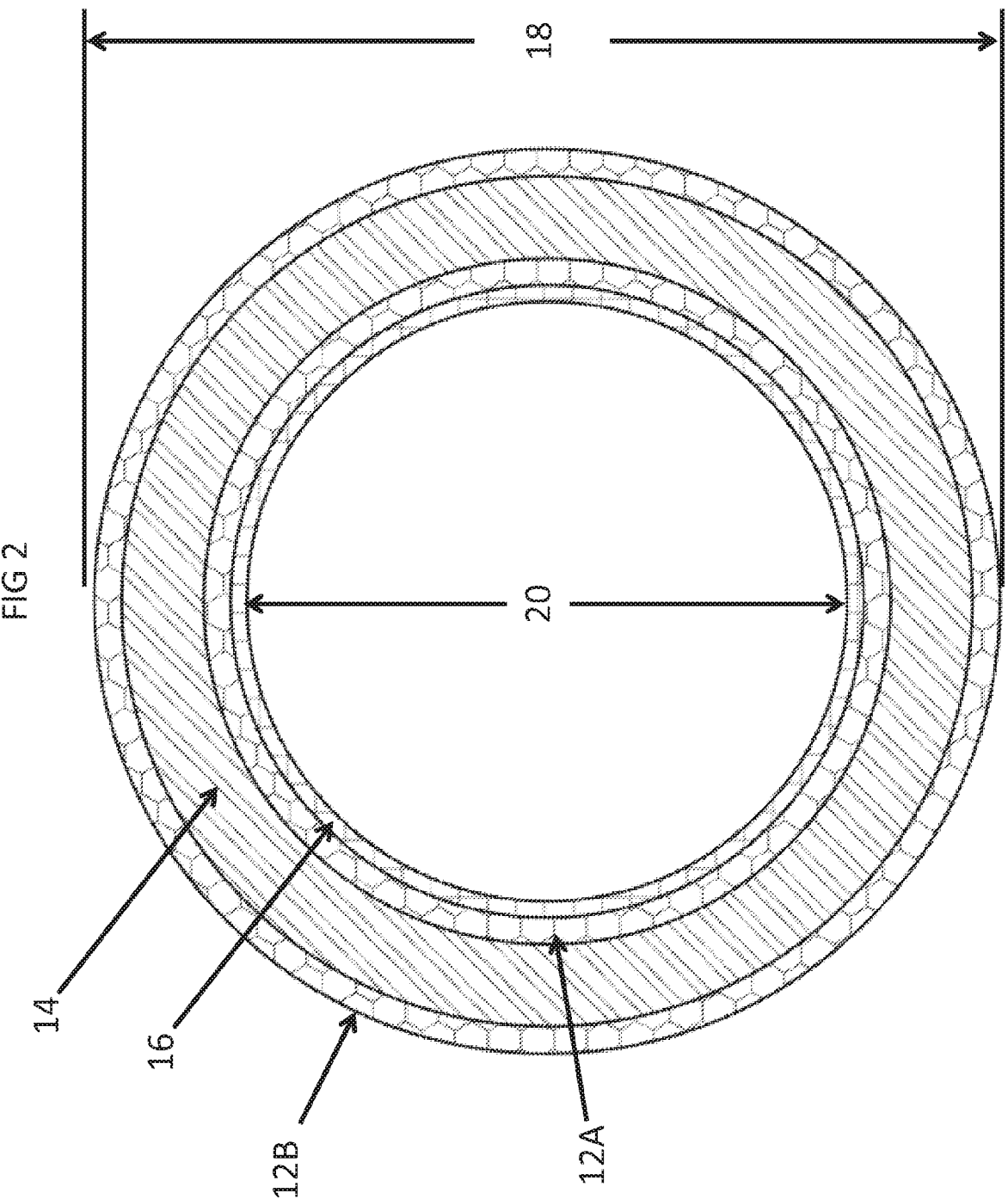

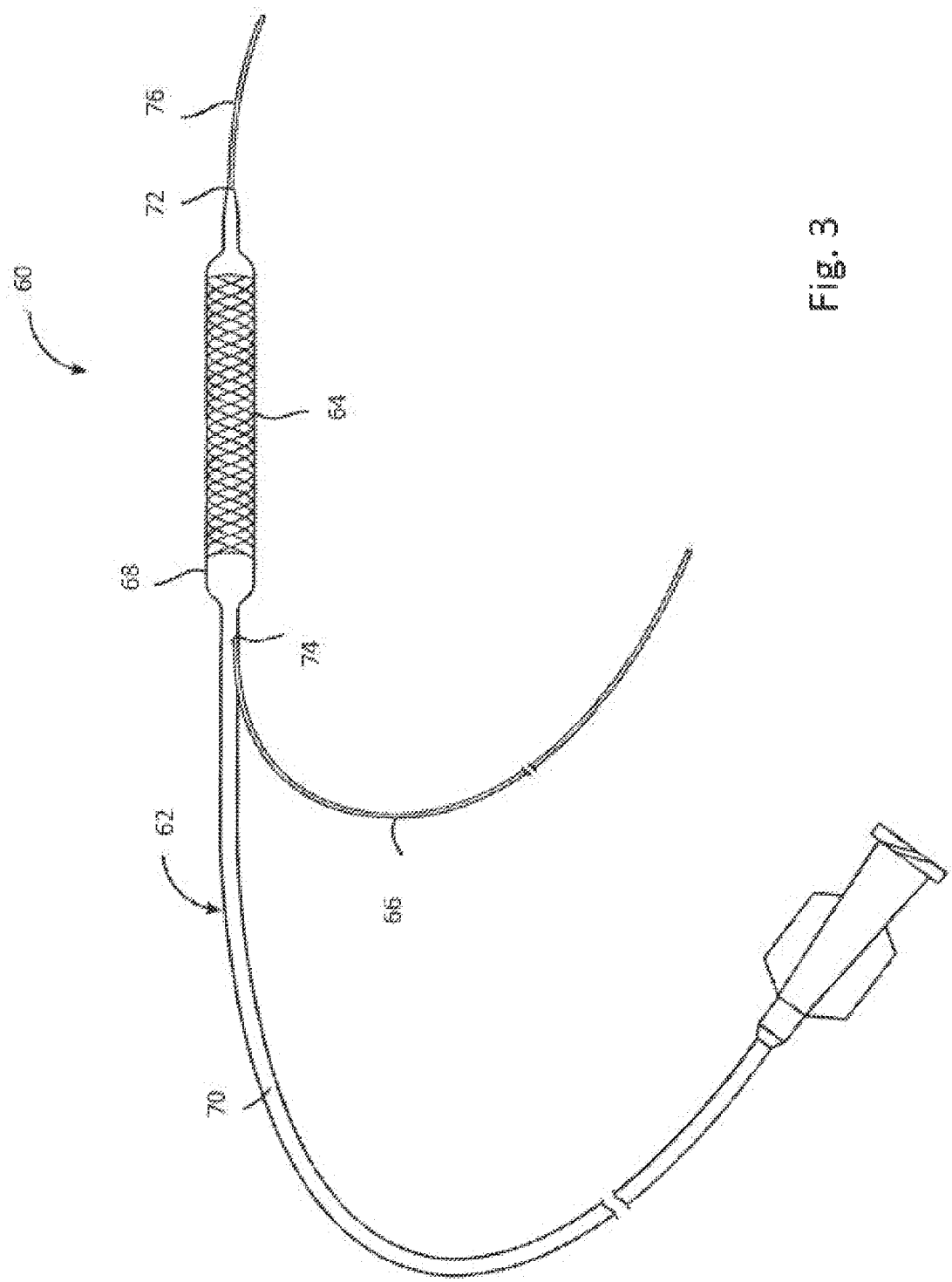

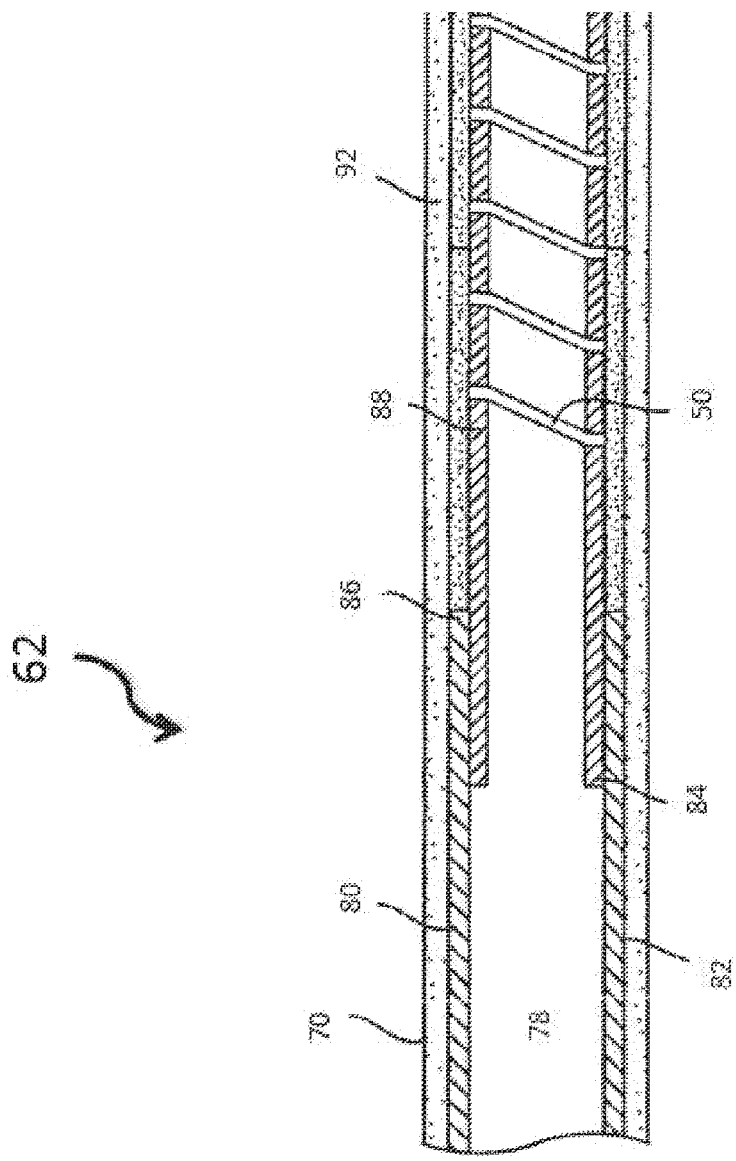

HYPOTUBE CONSTRUCTION

CROSS REFERENCE TO RELATED APPLICATION

This application is for entry into the U.S. National Phase under § 371 for International Application No. PCT/US2015/042676 having an international filing date of Jul. 29, 2015, and from which priority is claimed under all applicable sections of Title 35 of the United States Code including, but not limited to, Sections 120, 363, and 365(c), and which in turn claims the benefit of and takes priority from U.S. App. No. 62/030,435 filed on Jul. 29, 2014, and U.S. Provisional Application No. 62/055,712, filed on Sep. 26, 2014, the contents of which are hereby incorporated by reference.

BACKGROUND OF THE SYSTEM

Field of the System

The instant system relates generally to medical devices, and more particularly to a hypotube construction that may form part of a delivery device or catheter construction.

Description of the Related Art

Presently, numerous micro catheter designs exist that possess hypotubes utilized within the construction. In general, a hypotube is a long metal tube with micro-engineered features along its length. Additionally, a hypotube is a critical component of minimally-invasive catheters, utilized in conjunction with balloons and stents to open up clogged arteries for example. In many embodiments, the balloon portion of the catheter is attached to a head of the hypotube. Additionally, both full length hypotubes and partial length hypotubes (normally located at the proximal end of the catheter) may be utilized.

Typically hypotubes may possess some form of inside or internally located liner, which provides a low friction interface with the devices being pushed through the hypotube. These liners may slightly undersized as opposed to a laser cut hypotube so they slide inside a catheter or other medical device during manufacturing. In other embodiments, a hypotube may have a reinforcement which may give the liners more support and integrity as the catheters navigate the vasculature to a treatment location. In some instances, a polymer jacket is distributed on an outer diameter of the hypotube to provide a seal and also to minimize any surface roughness imparted by the laser cutting of the hypotube while still providing flexibility. As a result, this outer layer of the hypotube may also act as a tie layer to enable the application of coatings to enhance lubricity.

Moreover, medical devices such as hypotubes catheters may be subject to a number of often conflicting performance requirements such as flexibility, strength, minimized exterior diameter, maximized interior diameter, and the like. In particular, often times there is a balance between a need for flexibility and a need for strength. Therefore, a need remains for improved medical devices such as catheters that incorporate hypotube constructions which are configured for an optimal balance between flexibility, strength, and other desired properties.

SUMMARY OF THE SYSTEM

The instant apparatus and system, as illustrated herein, is clearly not anticipated, rendered obvious, or even present in any of the prior art mechanisms, either alone or in any combination thereof. A versatile system, method and series of apparatuses for creating and utilizing a hypotube system as part of a delivery device and other like systems is disclosed.

The present system pertains to improved medical devices providing advantages in flexibility, strength and other desired properties. Accordingly, an illustrative but non-limiting example of the present system may be found in a medical device such as a catheter that has an elongate shaft that includes a hypotube having cutting formed within the hypotube. The elongate shaft may define a lumen that extends within the elongate shaft.

Another illustrative but non-limiting example of the present system may be found in a medical device that includes a hypotube middle liner, a Teflon inner liner, and a powdered polymer coat. Thus, herein achieved is a system of a hypotube incorporated within a catheter to allow for a larger interior diameter working lumen than conventional designs while still maintaining the stiffness properties of the catheter shaft. These hypotube systems may be utilized in Neurovascular, Peripheral and cardiovascular procedures and/or in any other nonvascular procedure requiring a catheter which offers the largest interior diameter profile while also providing the lowest outer diameter profile possible.

It is an object of the present system to provide a hypotube with a customizable stiffness profile along its length to allow for a multitude of applications.

It is further object of the present system to provide a hypotube with a low friction interior surface.

It is a further object of the present system to provide a hypotube encapsulated in a dip coated polymer allowing for lower wall thickness.

It is a further object of the present system to provide a hypotube with a low wall thickness to allow for easier maneuverability and increased usages during medical procedures.

It is a further object of the present system to maintain superior stiffness properties overtime while exposed to the internal body temperature of an individual during a medical procedure.

It is a further object of the present system to provide a hypotube with a stiff proximal region to allow for increased pushability of a catheter incorporating the hypotube system.

It is a further object of the present system to provide a hypotube with a soft distal region for increased maneuverability during a medical procedure.

It is a further object of the present system to provide a hypotube for use in a variety of catheter applications.

Therefore, through the construction of the hypotube it is possible to achieve superior stiffness and support while also eliminating any issues relating to the softening of the hypotube body as a function of time exposed to an individual's internal body temperature during a medical procedure. A user may choose any cut pattern to provide the stiffness profile desired and achieve this stiffness with a wall thickness that is thinner than conventional braided or coiled constructions.

Further, the hypotube catheter shafts may be made from nitinol. Shafts made from nitonol tend to be an excellent choice for minimally-invasive catheter procedures because they can be designed with varying degrees of trackability and torque. This design flexibility allows the hypotube to be made to resist kinking in the most intricate, demanding medical procedures.

There has thus been outlined, rather broadly, the more important features of a hypotube construction and incorporation into a delivery device so the description thereof that follows may be better understood, and in order that the present contribution to the art may be better appreciated. There are additional features of the system that will be described hereinafter and which will form the subject matter of the claims appended hereto.

In this respect, before explaining at least one embodiment of the system in detail, it is to be understood that the system is not limited in its application to the details of construction and to the arrangements of the components set forth in the following description or illustrated in the drawings. The system is capable of other embodiments and of being practiced and carried out in various ways. Also, it is to be understood that the phraseology and terminology employed herein are for the purpose of description and should not be regarded as limiting.

These together with other objects of the system, along with the various features of novelty, which characterize the system, are pointed out with particularity in the claims annexed to and forming a part of this disclosure. For a better understanding of the system, its operating advantages and the specific objects attained by its uses, reference should be made to the accompanying drawings and descriptive matter in which there are illustrated preferred embodiments of the system.

BRIEF DESCRIPTION OF THE DRAWINGS

The system may be more completely understood in consideration of the following detailed description of various embodiments of the system in connection with the accompanying drawings, in which:

FIG. 1A is a simple cross-sectional view shown lengthwise of a hypotube in accordance with one embodiment of the present system.

FIG. 2 is a cross-sectional view shown along line 5-5 of the hypotube shown in FIG. 1A, in accordance with one embodiment of the present system.

FIG. 3 illustrates a side perspective view of one example of a known in the art catheter system.

FIG. 5 illustrates a cross-sectional view of a hypotube contained within the catheter system in FIG. 3 possessing a dip-coated polymer layer within a plurality of interstices.

Figure 1B:
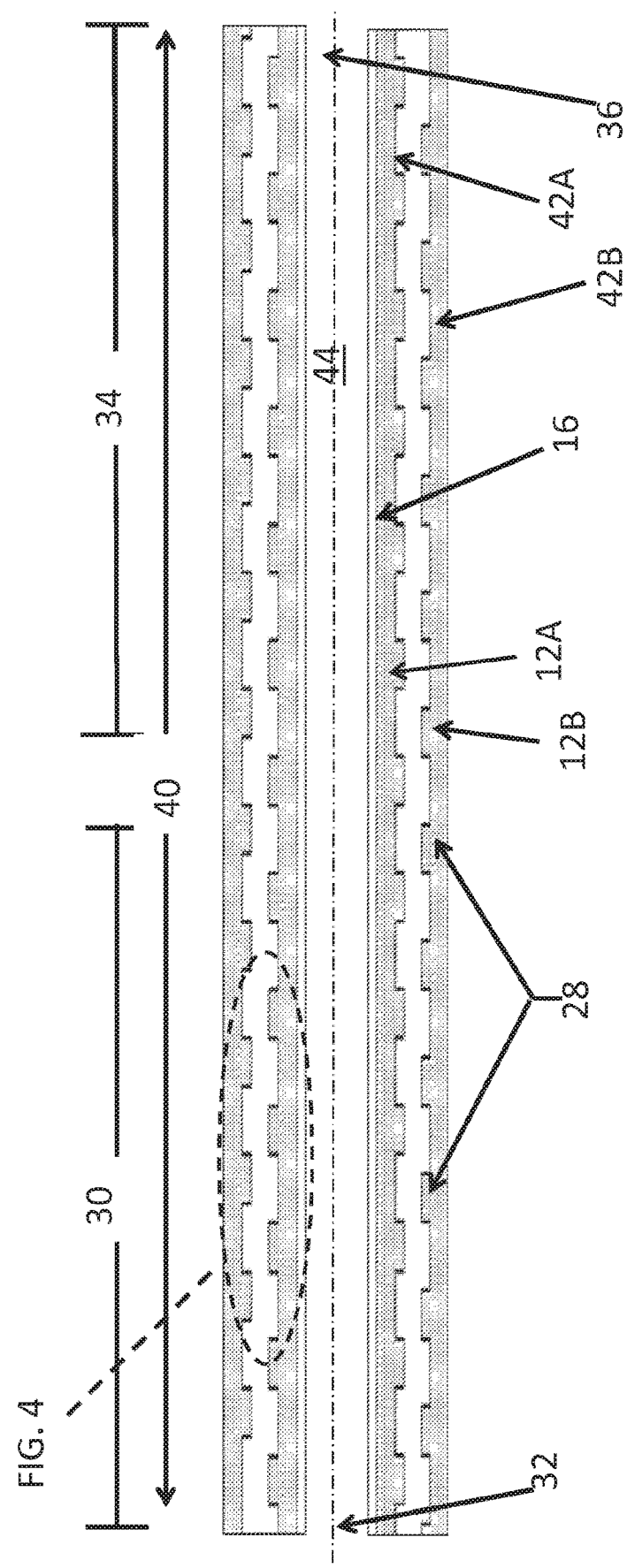
FIG. 1B is a detailed cross-sectional view shown lengthwise of a hypotube in accordance with one embodiment of the present system.

While the system is amenable to various modifications and alternative forms, specifics thereof have been shown by way of example in the drawings and will be described in detail. It should be understood, however, that the intention is not to limit the system to the particular embodiments described. On the contrary, the intention is to cover all modifications, equivalents, and alternatives falling within the spirit and scope of the system.

DETAILED DESCRIPTION OF THE SEVERAL EMBODIMENTS

For the following defined terms, these definitions shall be applied, unless a different definition is given in the claims or elsewhere in this specification. All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed system.

FIG. 1A illustrates a simple cross-sectional view shown lengthwise of a hypotube 10, wherein the hypotube 10 preferably is utilized in construction with micro-catheter designs (see FIG. 3). In one embodiment, the hypotube system 10 comprises a pair of polymer layers 12A and 12B, wherein the pair of polymer layers 12A and 12B surround a hypotube body 14. Additionally, a liner 16 may be secured against an inside surface (see FIG. 1B) of the hypotube body 14. In one embodiment, a first polymer layer 12A encapsulates the inside surface of the hypotube body 14, while a second polymer layer encapsulates an outside surface (see FIG. 1B) of the hypotube body 14. Furthermore, the liner 16 is secured against the second polymer layer 12B on the inside surface of the hypotube body 14.

The polymer layers 12A and 12B may be formed of any suitable polymeric material. In particular embodiments, the polymer layer 12 is formed of a material such as the ELAST-EON™ materials commercially available from AORTECH BIOMATERIALS, of Australia. The ELAST-EON™ materials generally are polyurethanes that include a polysiloxane component. While these materials encompass both elastomeric and non-elastomeric polymers, elastomeric polymers are useful in particular embodiments of the present system. In some instances, useful elastomeric polymers may exhibit an elongation of at least about 500 percent.

FIG. 1B illustrates a more detailed cross-sectional view shown lengthwise of a hypotube, 10. The hypotube system 10 comprises the pair of polymer layers 12A and 12B, wherein the polymer layers 12A and 12B surround the hypotube body 14. In another embodiment, a cut pattern 28 (see FIGS. 4B-4D for more detail) may be formed within the hypotube body 14; the cut pattern 28 may be cut in a number of ways to provide a desirable stiffness profile to a user. Different cut patterns may impart different degrees of support at specific sections along the length of the hypotube 10. Types of cut patterns 28 include, but are not limited to, C-cuts, spiral cuts, interrupted spiral cuts which may be varied numerous ways in a cut pitch or cut density to provide any stiffness profile desired in a catheter.

The hypotube 10 preferably comprises a proximal region 30 defining a proximal end 32, and a distal region 34 defining a distal end 36. The hypotube 10 may be cut in any number of ways to provide a desirable stiffness profile over an entire working length 40 of the hypotube 10. The cut pattern 28 may comprise any number of variations to impart different degrees of support at specific sections along the length 40 of the hypotube 10.

The hypotube body 14 further comprises an inside surface 42A and an outside surface 42B; preferably the inside surface 42A faces a lumen 44 formed by the hypotube body 14. In one embodiment, the liner 16 is placed against the inside surface 42A of the hypotube body 14 and secured in place by the first polymer layer 12A. The liner 16 may be a low friction material which provides a low friction interface desired to allow a variety of medical devices to be pushed through the hypotube 10 during a medical procedure.

In one embodiment, the liner 16 is a material which includes, but is not limited to: Teflon, PD Slick (i.e. a blend of PTFE and polyimide), a high density polyethylene or any other similar low friction materials. PTFE, polytetrafluoroethylene may be used as a lubricant-like material and reduce friction. When used in hypotube structures, PTFE has a low coefficient of friction for ease of navigation in intravenous procedures. A wide variety of coating technologies are available to maximize hypotube trackability including the PTFE coatings and polymer jackets.

In yet another embodiment, the hypotube 10 further comprises a pair of dip-coated polymer layers 12A and 12B, wherein the polymer layers 12A and 12B is preferably a solution that encapsulates a plurality of interstices 50 (see FIG. 4) located on the inside surface 42A and outside surface 42B of the hypotube body 14 created by the cut pattern 28. Furthermore, the polymer layers 12A and 12B preferably serve the dual purpose of providing a smooth outside surface 42B to the hypotube 10, while at the same time securing the liner 16 in place against the inside surface 42A of the hypotube body 14.

FIG. 2 illustrates a cross-sectional view along line 5-5 of the hypotube 10 shown in FIG. 1, wherein the hypotube 10 possesses an inside diameter 20 and a corresponding outside diameter 18. In practice, medical practitioners desire a larger inside diameter 20 working lumen 44 while keeping the outside diameter 18 of the hypotube 10 as close to the inside diameter 20 as possible to create a larger area for medical devices to pass through. The problem with this type of construction utilizing traditional catheter designs is through the expense of wall thickness which in turn affects shaft stiffness. Typically the longer a medical procedure case takes, traditional braided polymer catheters soften and lose their support properties.

The instant system eliminates these issues by providing a hypotube 10 construction, wherein the thickness of the inside diameter 20 and the outside diameter 18 is nearly identical, while being able to possess superior stiffness and flexibility properties.

Preferably, the liner 16 possesses a thickness in the range of 0.00025 inches to 0.001 inches, and more preferably possesses a thickness of one-one thousandth of an inch. Moreover, in one embodiment, the diameter of the lumen 44 is roughly seven-one hundredths of an inch; therefore, in practice the inside diameter 20 of the hypotube body 14 is almost identical to the diameter of the lumen 44 as the thickness of the liner 16 and the polymer layer 12 between the liner 16 and the inside surface 42A of the hypotube body 14 is minimal. In a preferred embodiment, the ratio of the thickness of the outer diameter 18 to the thickness of the inner diameter is in the range of 1.15:1 to 1.5:1.

In further embodiments, the hypotube may possess a range in the stiffness profile wherein the stiffest profile would equate to an uncut stainless steel tube (located near the proximal region 30) to as flexible as desired, which may be a function of the softest durometer polymer utilized (around 65 A on the durometer scale) combined with a high density cut pattern 28 (located near the distal region 34) which the hypotube body 14 may tolerate (distally 34). In yet another embodiment, the stiffness profile of the hypotube 10 may be in the range of 65 A to 75 D in accordance with the durometer scale as known in the art.

In further embodiments of the hypotube 10, the thickness of the hypotube body 14 may be in the range of one one-thousandths (0.001) of an inch to three one-thousandths (0.003) of an inch. Additionally, the first polymer layer 12A preferably includes a thickness in the range of five ten-thousandths (0.0005) of an inch to fifteen ten-thousandths of an inch (0.0015), and more preferably one one-thousandth of an inch (0.001) to fifteen ten-thousandths (0.0015) of an inch. Moreover, the second polymer 12B preferably includes a thickness in the range of three ten-thousandths (0.0003) of an inch to three thousandths (0.003) of an inch. Lastly, the lumen 44 of the hypotube body 14 may have an inner diameter 20 in the range of thirty-four ten-thousandths (0.0034) of an inch to thirty-six ten-thousandths (0.0036) of an inch; conversely the outer diameter 18 of the hypotube 10 may be in the range of forty-one ten thousandths (0.0041) of an inch to forty-three ten thousandths (0.0043) of an inch.

In one embodiment, the hypotube body 14 is preferably constructed of a material including, but not limited to stainless steel, cobalt chrome, nitinol, and any similar metallic compound which is not polymeric in nature. In other embodiments, part or all of the hypotube body may be formed of a metal or a metal alloy. Some examples of suitable metals and metal alloys include stainless steel, such as 304V, 304L, and 316L stainless steel; alloys including nickel-titanium alloy such as linear elastic or superelastic (i.e. pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 825; or the like; or other suitable material. The particular material used can be chosen in part based on the desired characteristics of the hypotube body 14, for example flexability, pushability, torqueability, and the like.

In even further embodiments, the hypotube body may be formed from a superelastic or linear elastic nickel-titanium alloy, for example, linear elastic or superelastic (i.e. pseudoelastic) nitinol.

Within the family of commercially available nitinol alloys, is a category designated "linear elastic" which, although is similar in chemistry to conventional shape memory and superelastic varieties, exhibits distinct and useful mechanical properties. By skilled applications of cold work, directional stress, and heat treatment, the wire is fabricated in such a way that it does not display a substantial "superelastic plateau" or "flag region" in its stress/strain curve. Instead, as recoverable strain increases, the stress continues to increase in an essentially linear relationship until plastic deformation begins. In some embodiments, the linear elastic nickel-titanium alloy is an alloy that does not show any martensite/austenite phase changes that are detectable by DSC and DMTA analysis over a large temperature range.

Preferably, the hypotube body 14 is constructed of a higher modulus metal which allows for a thinner hypotube body 14 construction which may be utilized to achieve a higher stiffness profile of the hypotube 10. Furthermore, the hypotube body 14 may comprise a cut pattern 28 including, but not limited to C-cut, spiral cut, interrupted spiral, and any combination/blend thereof. Additionally, the cut pattern 28 may vary along the length 40 of the hypotube body 14 such that the spacing of the cut pattern 28 in one embodiment may be equidistantly disposed along the length 40, whereas in another embodiment the spacing between the cut pattern 28 may be random or in a specified pattern that provides for unequal spacing. Additionally, the cut pitch and/or cut density of the cut pattern 28 may vary along the length 40 of the hypotube body 14 to incorporate various stiffness profiles depending on the medical procedure and requirement by physicians. Lastly, the polymer layers 12A and 12B may be a polymer including, but not limited to PEBAX, nylons, polyurethanes and other polymers that possess similar properties. In one embodiment, the polymer layers 12A and 12B may be a material that may be dissolved in solution and subsequently applied to the hypotube body 14 and liner 16 via a dip-coating process.

FIG. 3 illustrates a known in the art catheter system 60 which may incorporate the hypotube 10 of the present system; in this embodiment the catheter system 60 comprises a catheter 62 (shown schematically), a stent 64, a guidewire 66, and an expandable balloon 68, with the balloon 68 in an inflated or deflated configuration. In a deflated or delivery configuration, the balloon 68 and stent 64 will have an outer diameter close to the outer diameter of a shaft 70 of the catheter 62. The catheter 62 includes a distal guidewire portion 72 at a distal end 76 of the catheter 62 and a proximal guidewire portion 74 proximal of the balloon 64.

Figure 4A:
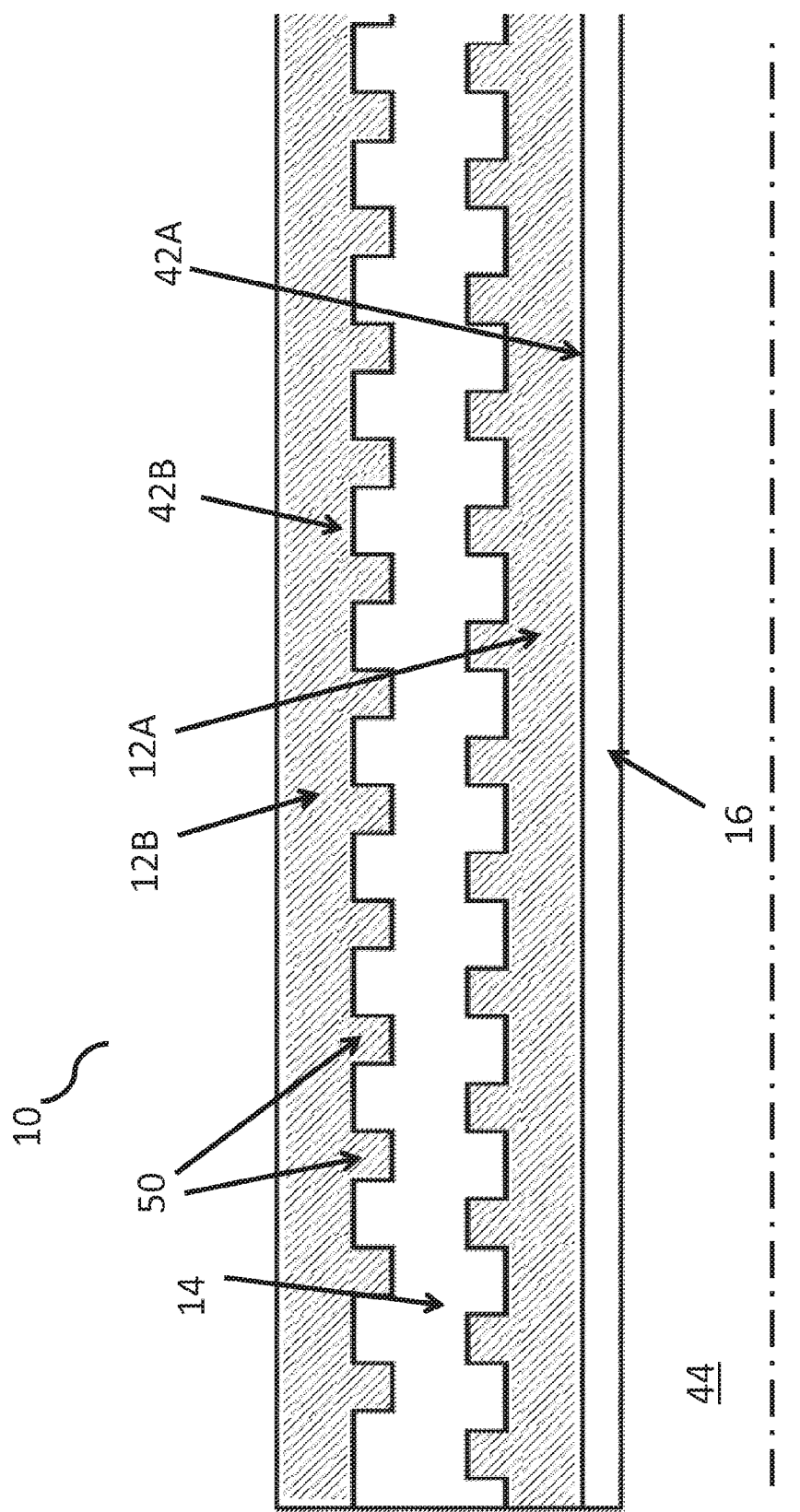
FIG. 4A illustrates an exploded longitudinal cross-sectional view of a portion of the hypotube system shown in FIG. 1B.

FIG. 4A illustrates an enlarged cross-sectional view taken from the dotted circle in FIG. 1B. The hypotube 10 further comprises a pair of polymer layers 12A and 12B, wherein the polymer layers 12A and 12B are preferably dip-coated and is a solution that encapsulates a plurality of interstices 50 created by the cut pattern 28.

The hypotube system preferably possesses a desired cut pattern 28 (see FIG. 1B) to provide the stiffness profile wanted and to achieve this stiffness with a wall thicknesses that is thinner than conventional braided or coiled constructions. Types of cut patterns 28 include, but are not limited to, C-cuts, spiral cuts, interrupted spiral cuts which may be varied numerous ways in a cut pitch or cut density to provide any stiffness profile desired in a catheter. Cuts used in an embodiment of the present system may be constant or varied depending upon the stiffness transition characteristics desired. For example, the pitch may be increased for more flexibility or decreased for less flexibility. Further, the cut pattern may extend partially through or all the way through the hypotube body. As stated, the cut pattern creates a set of interstices 50 filled with a low stiffness polymer that gives a smooth outer surface to the laser cut hypotube while at the same time securing a liner 16 in place. In this embodiment, the first polymer layer 12A and the second polymer layer 12B encapsulate the plurality of interstices 50 created by the cut pattern 28 in the hypotube body 14. In alternate embodiments, the cut pattern 28 and corresponding interstices 50 may be located on the outer surface 42B of the hypotube body 14 only, or the inside surface 42A of the hypotube body 14 only, so some combination thereof.

Additionally, the cut pattern 28 of the hypotube 10 may vary depending on the medical procedure involved and utilizing the hypotube 10. For example, the cut pattern 28 may vary as a function of the size of the medical device, location of the anatomy of a patient, and the length required to reach the target location from the insertion point.

One important element of the hypotube 10 described herein, is the ability to cut any stiffness profile over any discreet length, short or long. As such, it may be possible to start on the distal end of the hypotube body and go from stiff to soft and stiff again or any other permutation of those until the proximal end. However, the type of cut pattern 28 employed, and in turn the associated stiffness profile, may be anatomy specific and application specific. Moreover, in one embodiment, the maximum cut density per unit length will be dictated by how much the hypotube 10 being cut is affected by the heat generated by a laser, however in one embodiment a one hundredth (0.01) inch of gap separation in the consecutive cuts may be utilized.

Figure 4B:
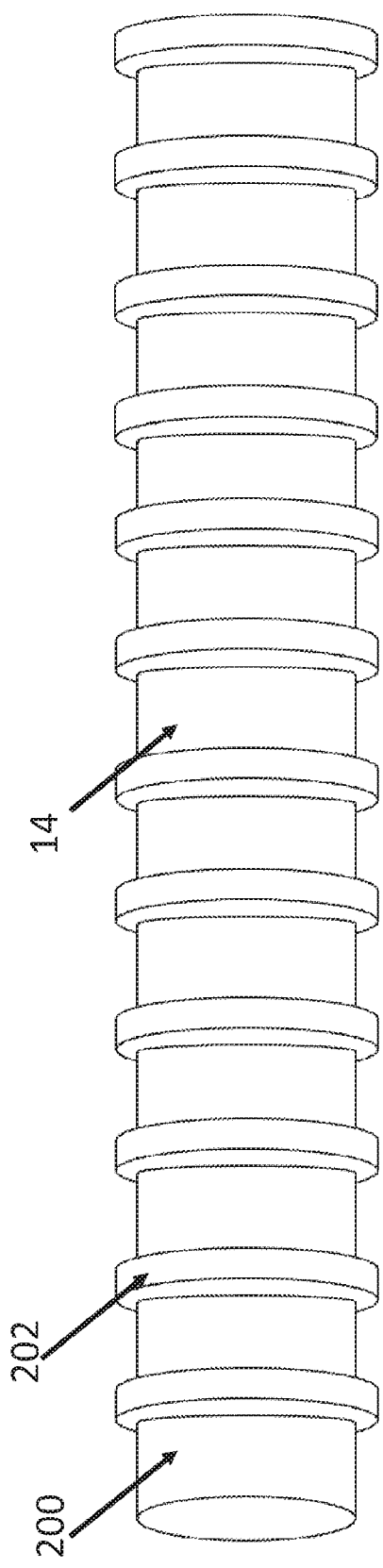
FIG. 4B illustrates a perspective view of one embodiment of the hypotube body.

FIG. 4B illustrates a perspective view of one embodiment of the hypotube body 14. In this embodiment the hypotube body 14 has a plurality of external grooves 202 that extend from a main body 200 of the hypotube body 14. In this embodiment the grooves 202 are externally oriented, however in other embodiments they may be internally oriented as depressions. In this embodiment the external grooves 202 are vertically oriented, however in other embodiments they may be oriented diagonally, horizontally or in a broken pattern.

Figure 4C:
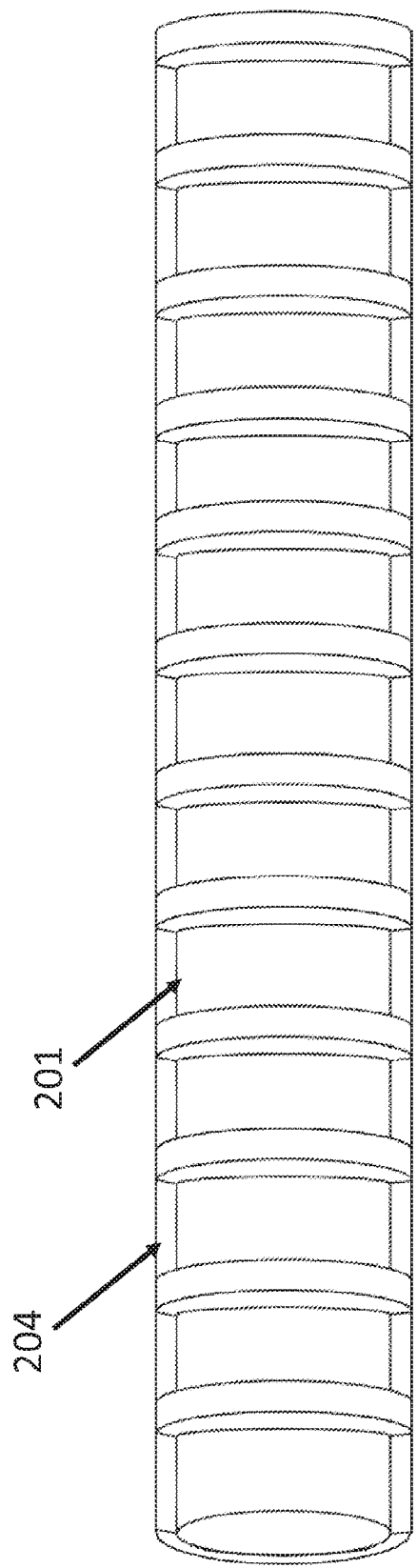
FIG. 4C illustrates a perspective cutaway view of one embodiment of the hypotube body with a polymer coating.

FIG. 4C illustrates a perspective cutaway view of an embodiment of the hypotube body 14 with a polymer coating 204. In this embodiment the polymer coating 204 fills a plurality of cavities 201 between the external grooves 202, however in other embodiments the polymer coating 204 may cover the entire hypotube body 14.

Figure 4D:
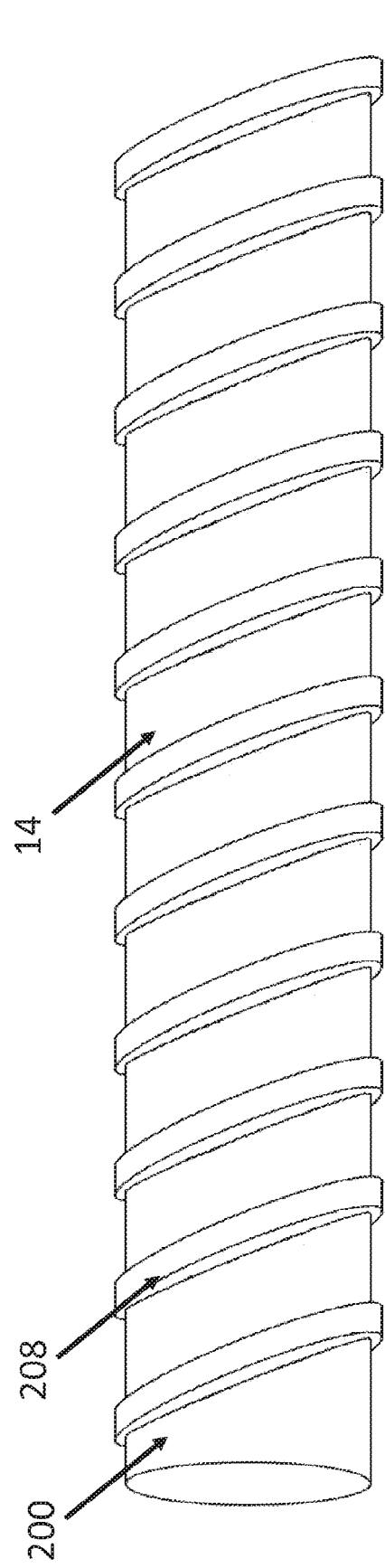
FIG. 4D illustrates a perspective view of an alternate embodiment of the hypotube body.

FIG. 4D illustrates a perspective view of an embodiment of the hypotube body 14. In this embodiment the hypotube body 14 has a plurality of diagonal grooves 208 that extend from the main body 200 of the hypotube body 14. In this embodiment the diagonal grooves 208 are externally oriented however in other embodiments they may be internally oriented as depressions. In this embodiment the diagonal grooves 208 are diagonally oriented, however in other embodiments they may be oriented vertically, horizontally or in a broken pattern.

Figure 4E:
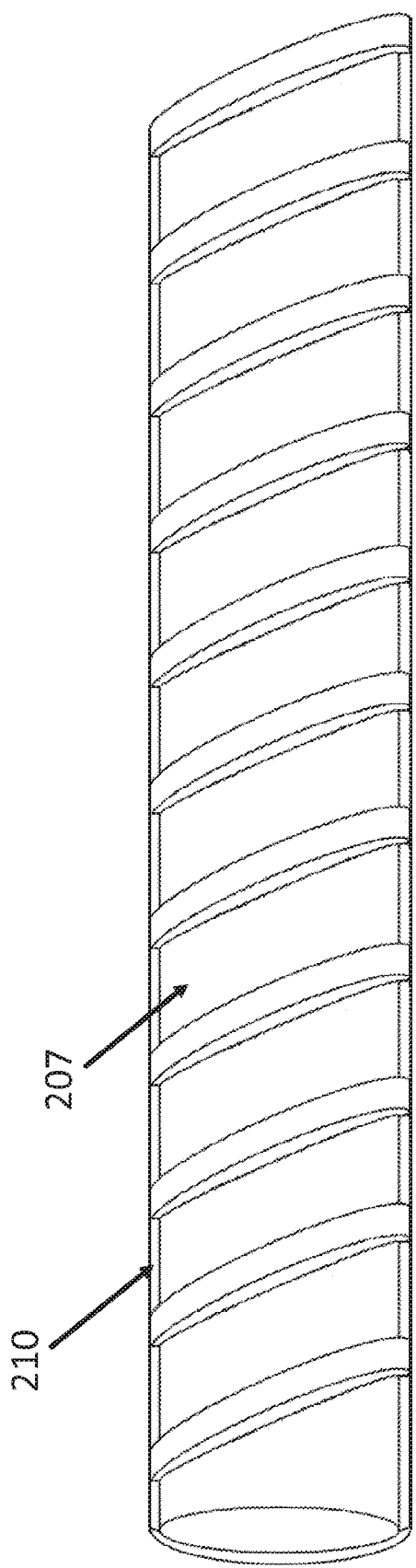
FIG. 4E illustrates a perspective cutaway view of one embodiment of the hypotube body with a polymer coating.

FIG. 4E illustrates a perspective cutaway view of an embodiment of the hypotube body 14 with a polymer coating 210. In this embodiment the polymer coating 210 fills a plurality of diagonal cavities 207 between the plurality of diagonal grooves 208, however in other embodiments the polymer coating 210 may cover the entire hypotube body 14.

Figure 4F:
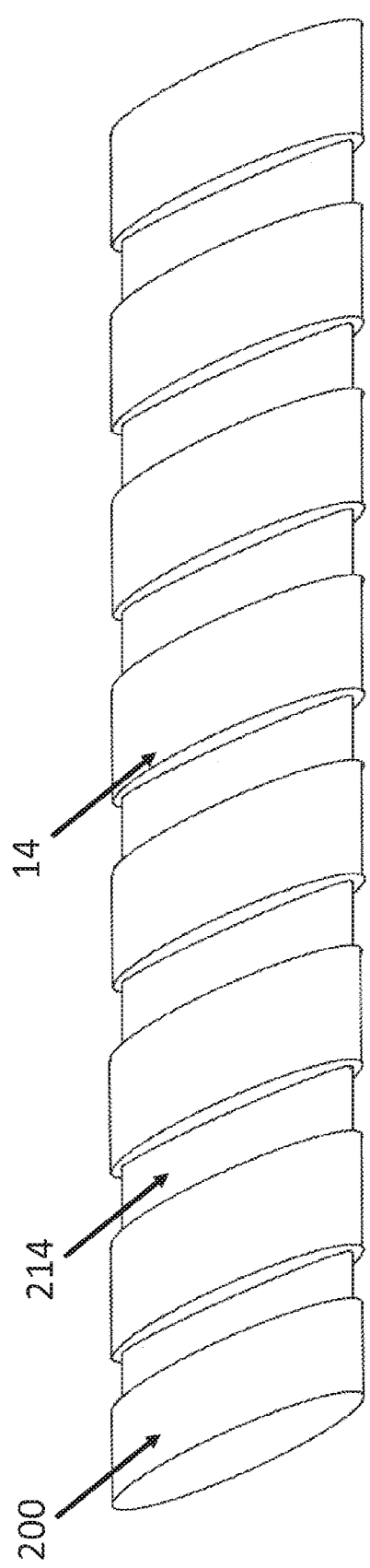
FIG. 4F illustrates a perspective view of an embodiment of the hypotube body.

FIG. 4F illustrates a perspective view of an embodiment of the hypotube body 14. In this embodiment the hypotube body 14 has a plurality of diagonal cuts 214 that extend from the main body 200 of the hypotube body 14. In this embodiment the plurality of diagonal cuts 214 are externally oriented however in other embodiments they may be internally oriented as depressions. In this embodiment the plurality of diagonal cuts 214 are diagonally oriented, however in other embodiments they may be oriented vertically, horizontally or in a broken pattern.

Figure 4G:
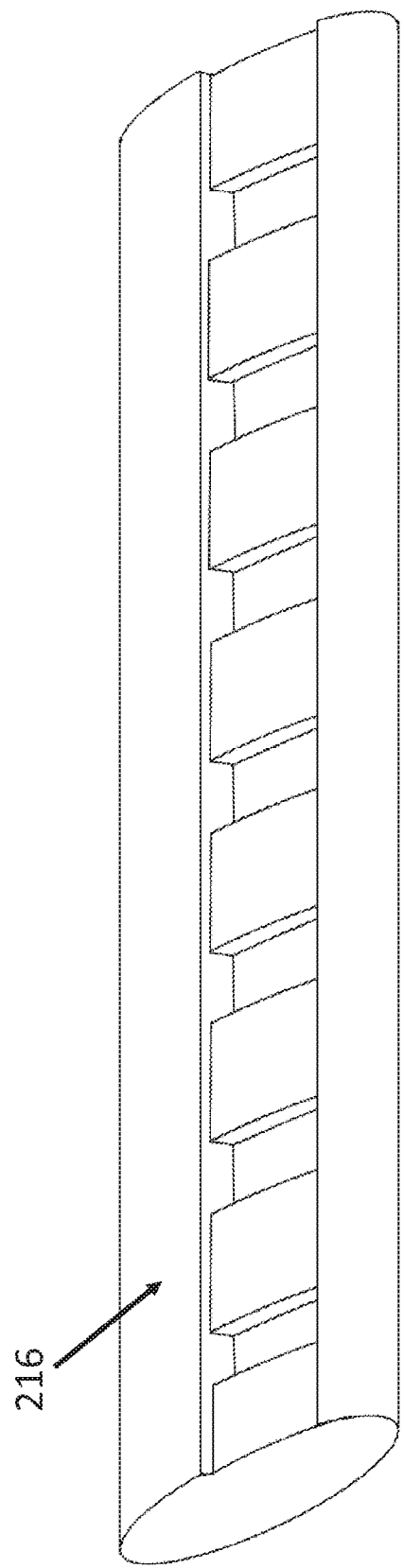
FIG. 4G illustrates a perspective cutaway view of an embodiment of the hypotube body with a polymer coating.

FIG. 4G illustrates a perspective cutaway view of an embodiment of the hypotube body 14 with a polymer coating 216. In this embodiment the polymer coating 210 fills the plurality of diagonal cuts 214 and the entire hypotube body 14.

FIG. 5 illustrates a longitudinal cross-sectional view of a portion of the catheter 62 illustrated in FIG. 3, incorporating yet another embodiment of the hypotube system. The catheter shaft 70 includes a hypotube shaft 80 including a proximal portion 82 and a distal portion 88, with the proximal 82 and distal 88 portions being joined together near the distal end 86 of the proximal portion and the proximal end 84 of the distal portion 88. An inflation lumen 78 extends through the hypotube shaft 80 into an interior of the balloon 68. In an exemplary embodiment, the two portions of the hypotube 80 are joined at a telescoping connection, that is, the distal end 86 of the proximal portion 82 is positioned distally of the proximal end 84 of the distal portion 88, and one of the two portions has an outer dimension.

Another advantageous, optional feature of the present system includes that the hypotube 80 comprises one or more cuts 50 formed therein, which increases the flexibility of the hypotube in the area of the cut 50. By way of example and not of limitation, the shape of the cut 50 may be C-cut, spiral cut, interrupted spiral cut, as well as other shapes and orientations of one or more cuts 50, so that a desired stiffness profile may be achieved by a user of a catheter. Additionally, the cut 50, or the density of cuts 50, may be non-uniform, and advantageously may be formed so that the configuration of the cut 50 contributes to the increasing flexibility of the catheter shaft 70. The plurality of cuts form a cut pattern 28. By way of non-limiting example, a spiral cut, such as that illustrated herein, may be formed, e.g., by laser cutting.

Yet another advantageous, optional feature of the present system is the further inclusion of a polymer jacket 92 over the hypotube 80. By forming the jacket 92 of a polymer material, the catheter shaft 70 may be made fluid tight to the inflation fluid passing through inflation lumen 78, relatively low friction to assist in passing the catheter 62 through the vasculature of a patient, and the flexibility of the catheter shaft 70 may further be modified. More specifically, the jacket 92 may be formed of a material, and having thicknesses, so that the flexibility of the shaft 70 increases distally.

In practice, the hypotube 10 may form a catheter construction in the range of one-and-a-half to twenty French, and more preferably in the range of three to six French. Furthermore, in one embodiment, the proximal region 30 will possess a stiffer profile in comparison to the distal region 34, which will be softer in nature. As such, the stiffer proximal region facilitates better pushability while in turn the softer distal region 34 assists navigating a vessel tortuosity. However, in alternate embodiments, the stiffness profiles between the proximal end 32 and the distal end 36 may comprise an infinite number of profiles depending on the properties required for treating a specific disease where more or less support is required at certain locations over the length of the hypotube 10.

In alternate embodiments, the hypotube 10 in accordance with the present system, may be of any of variety of different catheters. In some embodiments, the hypotube 10 may be an intravascular catheter; examples of intravascular catheters include balloon catheters, atherectomy catheters, drug delivery catheters, stent delivery catheters, diagnostic catheters and guide catheters. Furthermore, the intravascular hypotube 10 may be sized in accordance with its intended use. Furthermore, the hypotube 10 may be utilized in a variety of procedures, including but not limited to: Neurovascular, Peripheral, Cardiovascular, and in any non-vascular procedure requiring a catheter which offers the largest inside diameter of the lumen 44 while keeping the outside diameter profile low.

Therefore, having the ability to deliver larger lumen devices with superior support profiles, physicians do not need to worry about having to insert a supporting sheath(s) over the guide catheter outside diameter for enhanced support or insert a stiff buddy wire inside the guide lumen to enhance its support. As such, the instant system provides a novel hypotube solution, for use with a variety of micro catheter designs, wherein the hypotube 10 allows for large catheters to behave as small catheters from a functionality and usage standpoint, and conversely to allow small catheters to behave as large catheters during use.

Figure 6:
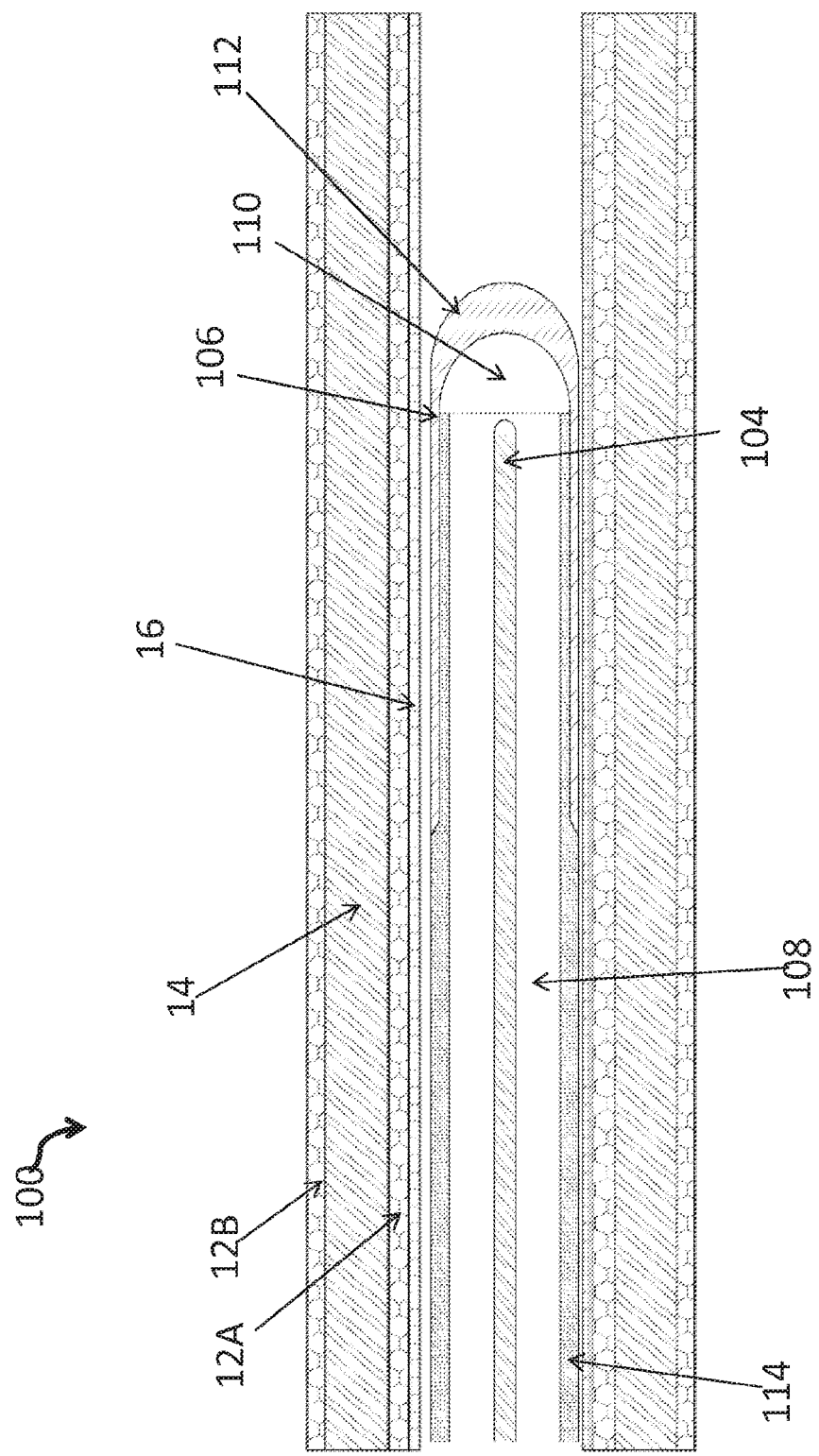
FIG. 6 illustrates a cross-sectional view of a hypotube incorporating a mandrel support guidewire within a cavity of the hypotube construction for the delivery of a medical device to a treatment area.

FIG. 6 illustrates one embodiment wherein a balloon with mandrel support guidewire is loaded within the hypotube body. The removable mandrel support guidewire 104 runs concentrically along the length of a reinforced single lumen shaft and is pushed through the hypotube body 14.

In one embodiment, within the hypotube body 14 is a reinforced single lumen shaft 108; a removable mandrel support guidewire 104; a bonded balloon 106 that is deflated; the bonded balloon 106 may include a bonded tip 110 and an attached soft atraumatic tip 112. The reinforced single lumen shaft 108 may be comprised of a reinforced polymer outer layer 114.

Furthermore, a distal head 112 of the guidewire 104 preferably remains free-floating relative to an extreme distal end of the catheter 100 but is anchored to the catheter 100 at a more proximal location (not shown). This anchoring helps ensure that the distal head of the guidewire 104 will not break off from the catheter 100 during use. Any suitable anchoring device may be used and is contemplated within the scope of the system.

Figure 7:
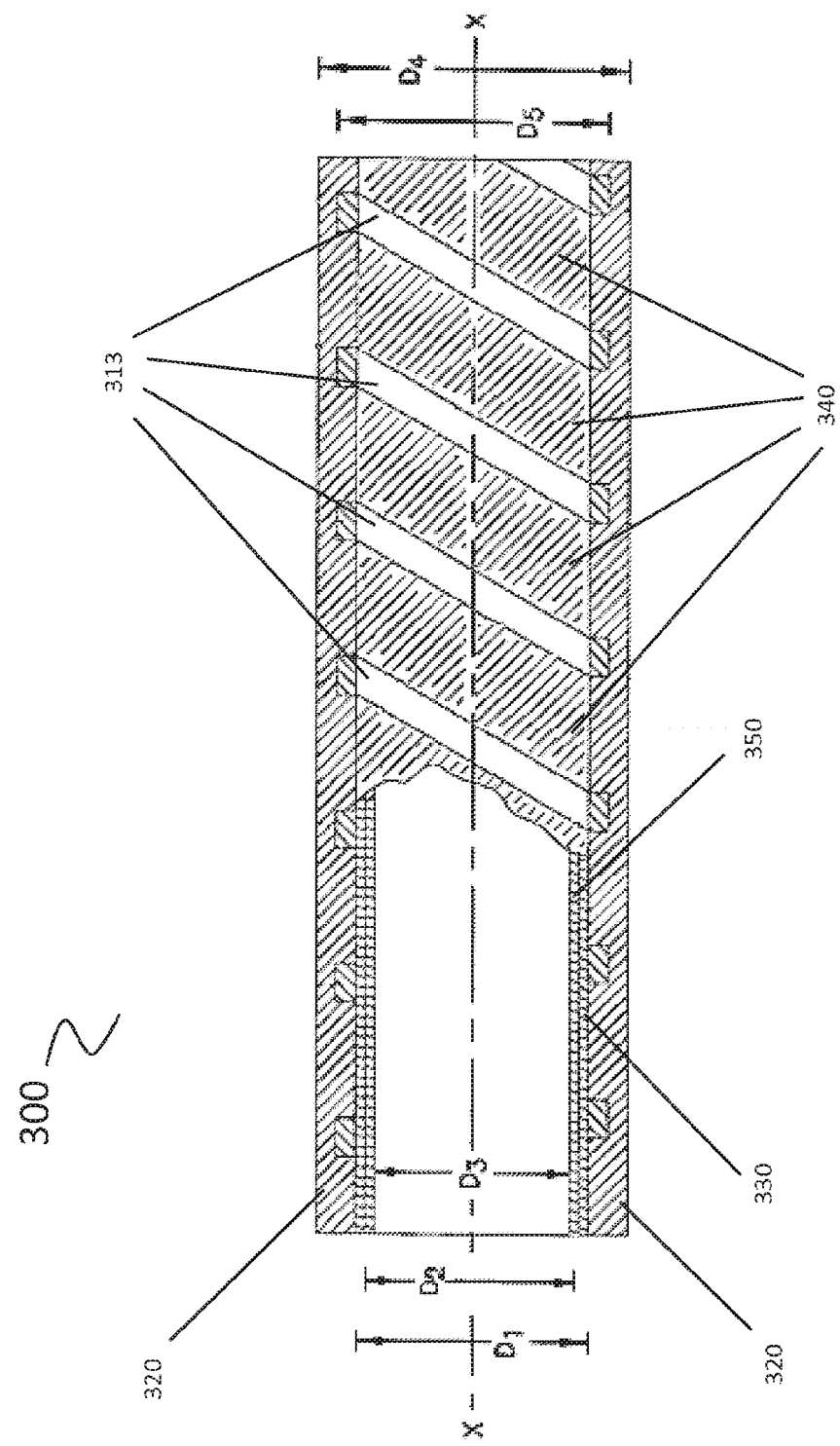
FIG. 7 illustrates a cross-sectional, longitudinal view of a longitudinal segment of one embodiment of the enhanced hypo-tube catheter system.

FIG. 7 illustrates a cross-sectional, longitudinal view of a longitudinal segment of one embodiment of the enhanced hypo-tube catheter system 300, wherein the base hypotube catheter 310 comprises a substantially spiral cut body. Similar to many other embodiments disclosed herein, the hypotube catheter system 300 further comprises an outer polymer layer 320, which may be a dip-coated polymer layer, wherein the outer polymer layer 320 comprises a solution that encapsulates the outside hypotube catheter surface.

The hypotube catheter system 300 further comprises a first inner polymer layer 330 which comprises a solution that encapsulates the inner hypotube catheter surface. The hypotube catheter system 300 further comprises an interstices polymer layer 340 wherein interstices polymer layer 340 comprises a solution that encapsulates the surfaces of the set, or plurality, of interstices 313 of the spiral cut hypotube body 300.

The hypotube catheter system 300 further comprises a second inner polymer layer 350, wherein the polymer layer may comprise a composition of polytetraflouroethylene (PTFE) or other Teflon™ derivative.

In conclusion, herein is presented a hypotube construction, preferably for use in forming a catheter. The system is illustrated by example in the drawing figures, and throughout the written description. It should be understood that numerous variations are possible, while adhering to the inventive concept. Such variations are contemplated as being a part of the present system.

What is claimed is:

1. A hypotube comprising:
   a hypotube body;

a pair of polymer layers, wherein a first polymer layer of the pair of polymer layers encapsulates an inside surface of the hypotube body, and wherein a second polymer layer of the pair of polymer layers encapsulates an outside surface of the hypotube body;

a liner, wherein the liner is secured to the inside surface of the hypotube body by the first polymer layer; and a cut pattern, wherein the cut pattern is formed on the hypotube body;

a plurality of interstices formed by the cut pattern on the hypotube body, wherein the interstices created by the cut pattern are filled with a low stiffness polymer of the second polymer layer creating a smooth outer surface; and a proximal and a distal region, wherein the proximal region possesses a stiffer profile in comparison to the distal region to allow for increased pushability and increased maneuverability;

wherein the hypotube compromises an outside diameter and an inside diameter with a ratio of thickness of the outside diameter to the inside diameter is in the range of 1.15:1 to 1.5:1;

wherein the inside surface of the hypotube body faces a lumen within the hypotube body.

2. The hypotube of claim 1, wherein the liner is a material selected from the group consisting of: polytetrafluoroethylene, a blend of polytetrafluoroethylene and polyimide, and a high density polyethylene.

3. The hypotube of claim 1, wherein the second polymer layer encapsulates the plurality of interstices on the hypotube body.

4. The hypotube of claim 1, wherein the hypotube body is a material selected from the group consisting of: stainless steel, cobalt chrome, and nitinol.

5. The hypotube of claim 1, wherein the hypotube body is constructed of a higher modulus metal to allow for a thinner hypotube body to achieve a higher stiffness profile of the hypotube.

6. The hypotube of claim 1, wherein the cut pattern is selected from the group consisting of: a c-cut, a spiral cut, an interrupted cut, and any combination/blend thereof.

7. The hypotube of claim 1, wherein the cut pitch and cut density of the cut pattern varies along a length of the hypotube to incorporate various stiffness profiles.

8. The hypotube of claim 1, wherein the low stiffness polymer of the second polymer layer is selected from the group consisting of: polyether block amide, nylons, and polyurethanes.

9. The hypotube of claim 1, wherein the hypotube forms a catheter construction in the range of one-and-a-half to twenty French.

10. The hypotube of claim 1, wherein the hypotube forms a catheter construction in the range of three to six French.

11. The hypotube of claim 1 possessing a stiffness profile between 65A to 75D in accordance with the durometer scale.

12. The hypotube of claim 1 wherein the liner comprises a thickness range of 0.00025 to 0.001 inches.

* * * * *